US00PP31402P3

(12) United States Plant Patent
Skelton

(10) Patent No.: US PP31,402 P3
(45) Date of Patent: Jan. 28, 2020

(54) ***ACTINIDIA* PLANT NAMED 'KZ03'**

(50) Latin Name: *Actinidia chinensis*
Varietal Denomination: KZ03

(71) Applicant: Donald Alfred Skelton, Rangiriri (NZ)

(72) Inventor: Donald Alfred Skelton, Rangiriri (NZ)

( * ) Notice: Subject to any disclaimer, the term of this patent is extended or adjusted under 35 U.S.C. 154(b) by 0 days.

(21) Appl. No.: 15/932,939

(22) Filed: May 22, 2018

(65) Prior Publication Data

US 2019/0364708 P1 Nov. 28, 2019

(51) Int. Cl.
*A01H 5/08* (2018.01)
*A01H 6/00* (2018.01)

(52) U.S. Cl.
USPC ..... Plt./156
CPC ..... *A01H 6/00* (2018.05)

(58) Field of Classification Search
USPC ..... Plt./156
See application file for complete search history.

(56) References Cited

PUBLICATIONS

UPOV hit on *Actinidia* plant named 'KZ03', ZA PBR PT8474, application date Mar. 7, 2018.*

* cited by examiner

*Primary Examiner* — Anne Marie Grunberg
(74) *Attorney, Agent, or Firm* — Cassandra Bright

(57) ABSTRACT

A new and distinct *Actinidia chinensis* plant named 'KZ02' is disclosed, characterized by a distinctive yellow inner pericarp and a mid-seasonal harvest time. The new variety bears fruit heavily and produces a consistently shaped oblong shaped fruit. The new variety is suitable for commercial production of kiwi fruit.

4 Drawing Sheets

Latin name of the genus and species: *Actinidia chinensis*.
Variety denomination: 'KZ03'.

BACKGROUND OF THE INVENTION

The new cultivar is a product of a planned breeding program under the direction of the inventor, Donald Alfred Skelton, a citizen of New Zealand. The seed parent is the unpatented, proprietary seedling variety *Actinidia chinensis* '91'. The pollen parent is the unpatented, proprietary seedling variety referred to as *Actinidia chinensis* '370a'. The crossing was made by the inventor during 1992.

Fruit of the new variety was first evaluated in 2008 with favorable results. After the first evaluation, semi-hardwood cuttings were made of 'KZ03' and were grafted onto seedling rootstocks of *A. deliciosa* during 2008. Evaluation, asexual propagation and grafting all first took place at a research nursery in North Waikato, New Zealand. Subsequent evaluations of the variety have shown the characteristics to be true to type.

SUMMARY OF THE INVENTION

The cultivar 'KZ03' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KZ03' These characteristics in combination distinguish 'KZ03' as a new and distinct *Actinidia chinensis* cultivar:

1. Heavy bearer.
2. Consistent oblong fruit shape.

3. Medium plant vigor.
4. Precocious.
5. Flowering late April, early May.
6. Inner pericarp coloration near Yellow 4A.

PARENT COMPARISON

The new variety is similar to the seed parent variety in some horticultural characteristics. However, the new variety differs in the following;

1. The new variety has an oblong fruit shape, compared to the ovoid parent fruit.
2. The new variety produces mature fruit during mid-season, compared to late season fruiting of the seed parent.
3. Fruit of the new variety is much larger than that of the seed parent
4. The new variety flowers mid-season, the seed parent flowers early season.

The new variety can be compared to the pollen parent variety, however, the plants clearly differ, as the new variety is a fruit producing female plant and the pollen parent is a non-fruiting male plant. Additionally, the new variety differs in the following;

1. The new variety flowers later than the pollen parent variety.
2. No fruit is produced by the pollen parent.

COMMERCIAL COMPARISON

The new variety is best compared to the commercial variety, 'ZESY002', U.S. Plant Pat. No. 22,355. 'KZ03' is similar to 'ZESY002' in many horticultural characteristics, however, 'KZ03' differs in the following:

1. Ploidy; the new variety is a diploid, 'ZESY002' is a tetraploid.
2. The new variety flowers mid-season, this comparator flowers late season.
3. The new variety produces fruit with a brighter yellow (4A) inner pericarp, compared to 8D of this comparator.

The new variety can be compared to the commercial variety 'Y368', U.S. Plant Pat. No. 20,721. 'KZ03' is similar to 'Y368' in many horticultural characteristics, however, 'KZ03' differs in the following:

1. The new variety flowers mid-season, this comparator flowers early season.
2. The new variety produces mature fruit mid-season, this comparator produces mature fruit early season.

BRIEF DESCRIPTION OF THE PHOTOGRAPHS

The accompanying photograph in FIG. 1 illustrates fruit harvested from 'KZ03'.

DETAILED BOTANICAL DESCRIPTION

Figure 1:
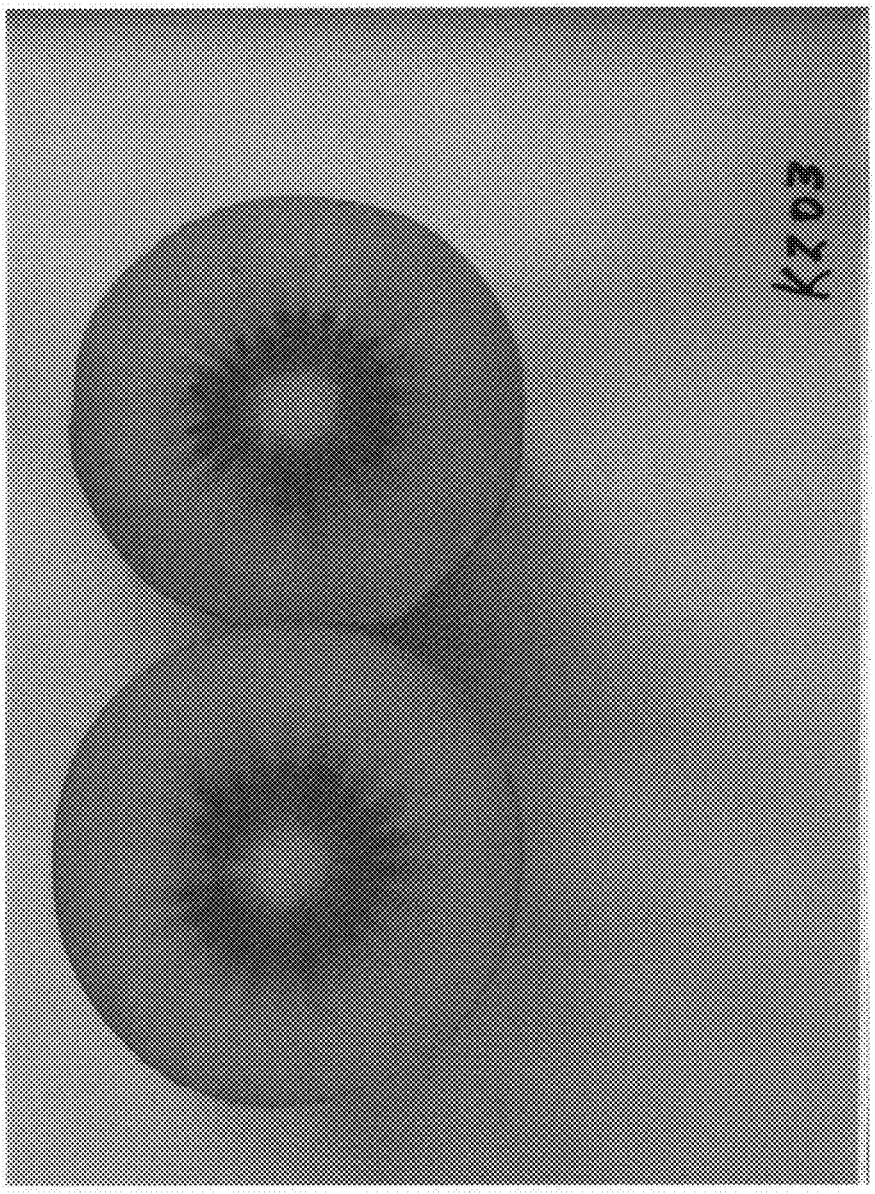
Figure 2:
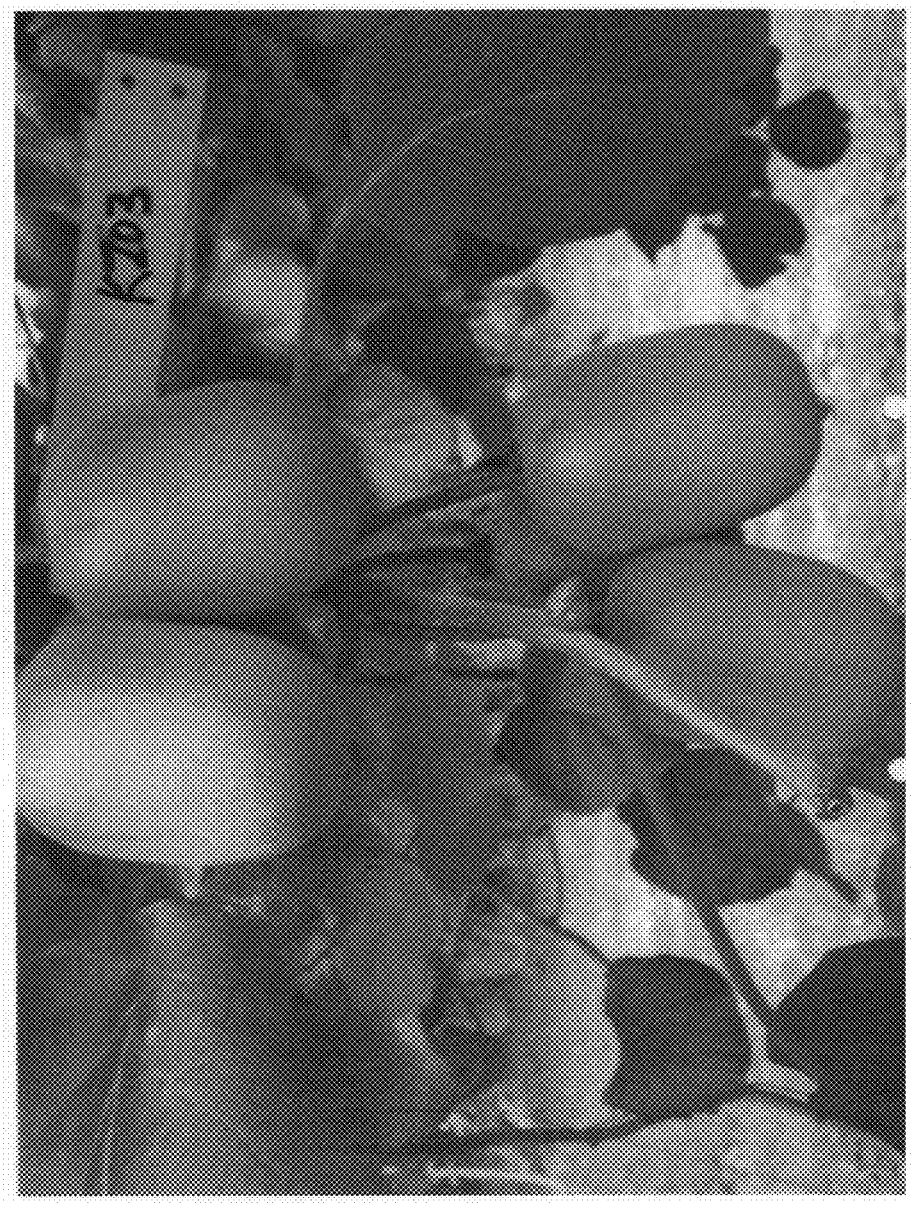
FIG. 2 illustrates in full color examples of typical fruits of 'KZ03', while on the plant, as well as typical foliage.
Figure 3:
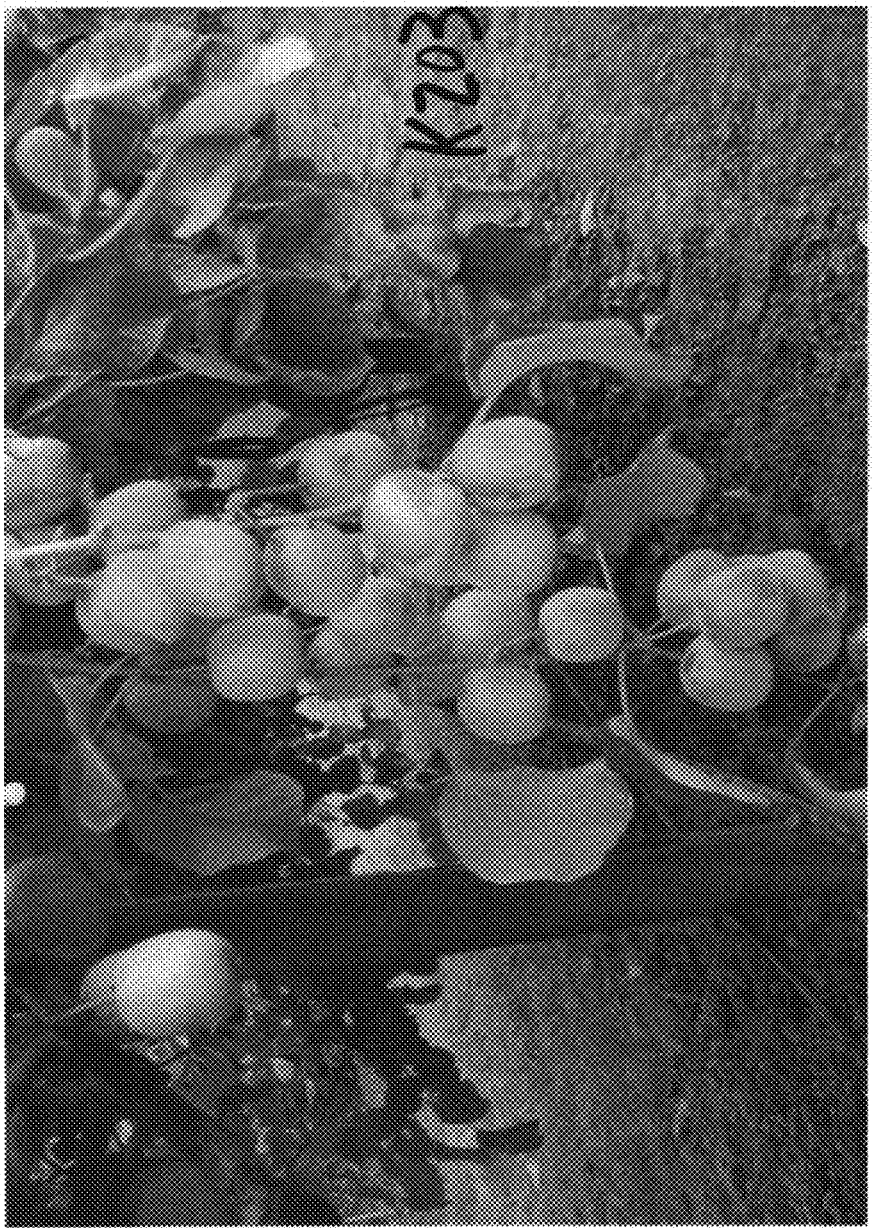
FIG. 3 illustrates the heavy bearing characteristics of the variety.
Figure 4:
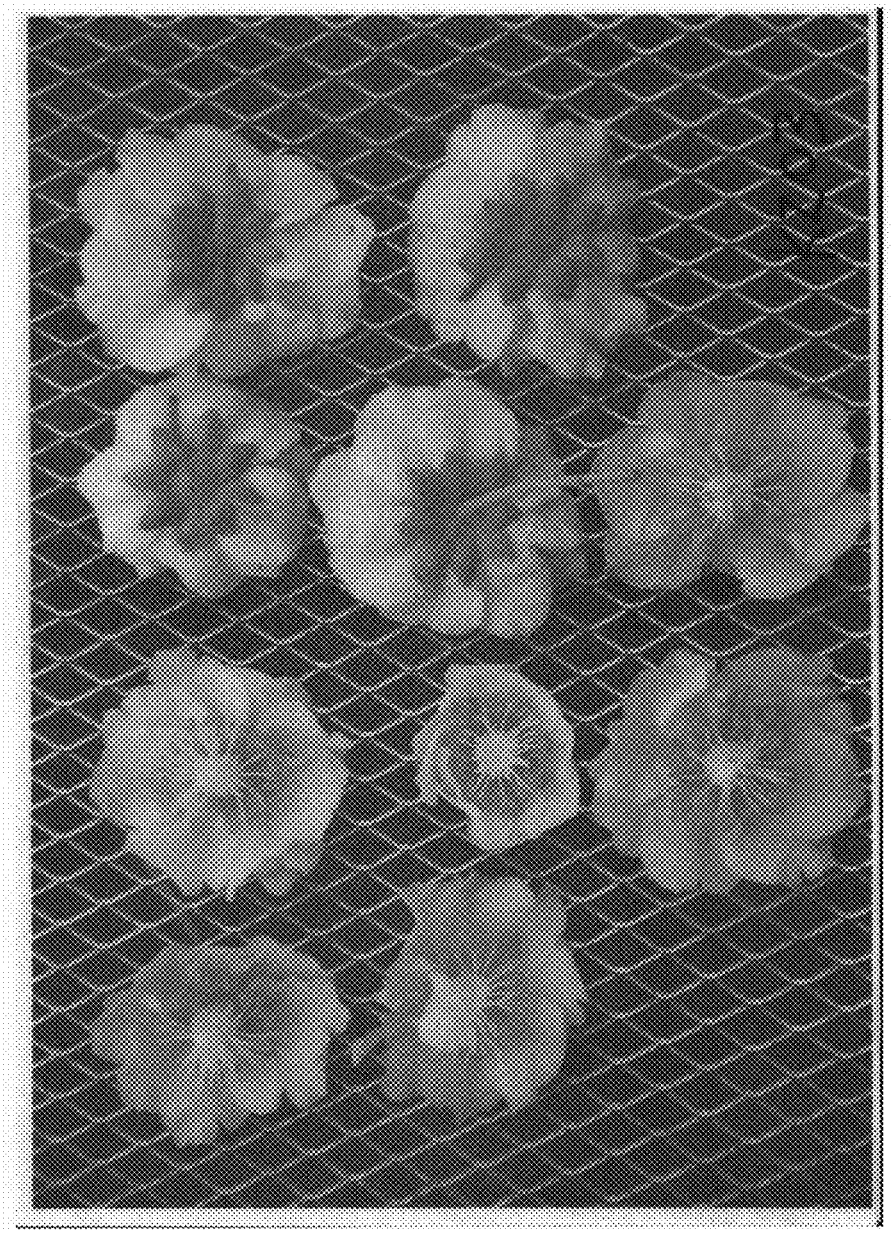
FIG. 4 shows the front and back sides of the flowers. The photographs were taken using conventional techniques and although colors may appear different from actual colors due to light reflectance it is as accurate as possible by conventional photographic techniques.

In the following description, color references are made to The Royal Horticultural Society Colour Chart 2007 except where general terms of ordinary dictionary significance are used. The following observations and measurements describe 'KZ03' plants grown outdoors under commercial trial conditions in Rangiriri, New Zealand. The growing temperature ranged from 10° C. to 30° C. during the day and −3° C. to 15° C. at night. Annual rainfall is approximately 125 cm per year. Measurements and numerical values represent an average of 10 typical plant types, measurements of foliage taken from mid June to mid August.

Botanical classification: *Actinidia chinensis* 'KZ03'.

PROPAGATION

'KZ03' can be successfully grafted onto rootstocks of *Actinidia deliciosa.*

PLANT

Age of the plant described: Approximately 10 years.
Sex expression: Female.
Ploidy: Diploid.
Average height: 2 m.
Average width: 5 m.
Vigor: Average.
Young shoot color: Near RHS 145A.
Young shoot texture: Glabrous.
Mature branch/shoot diameter: Average 1.5 cm.
Mature branch/shoot length: Average 200 cm.
Mature branch/shoot texture: Smooth.
Stem lenticels description:
*Length.*—Average 1.0 mm.
*Width.*—Average 0.1 mm.
*Density.*—Approximately 20 per 5 cm of stem.
Stem pith: Solid.
Leaf scar: Shallow.
Trunk diameter: Approximately 7.0 cm for a 10-year-old plant.
Trunk texture: Rough.
Trunk color: Near RHS 152D.

FOLIAGE

Leaf:
*Average length.*—Average range from 15 cm to 18 cm.
*Average width.*—Average range from 16 cm to 20 cm.
*Shape of blade.*—Retuse.
*Apex.*—Retuse.
*Base.*—Cordate.
*Margin.*—Slightly ciliate.
*Texture of top surface.*—Light pucker.
*Texture of under side.*—Non-pubescent.
*Color.*—Mature foliage upper side: Near RHS 137A. Mature foliage under side: Near RHS 138C.
*Petiole.*—Length: 11 cm. Pubescence: Nil. Color: Near RHS 142C.

FLOWER

*Flowers per inflorescence.*—1 to 4.
*Flower shape.*—Hemispherical.
*Bud color.*—Near RHS 145B.
*Bud shape.*—Oblong.
*Bud break.*—Medium to late.
*First flower.*—October 15.
*Diameter.*—Average 6-5 cm.
*Depth.*—Average 3-8 cm.
*Petal quantity.*—8 to 10.
*Petals overlapping.*—Yes.
*Petals.*—Length: Approximately 3.2 cm. Width: Approximately 2.2 cm. Shape: Spatulate. Aspect: Slightly undulating. Margin: Entire, with infrequent irregular shallow crenations. Texture: Glabrous, all surfaces. Base: Attenuate. Apex: Obtuse.
*Petals.*—Color: Upper Surface: Near RHS 159D. Lower Surface: Near RHS 159D.
*Filament color.*—Near RHS 157D.
*Anther color.*—Near RHS 163B.
*Attitude of styles.*—Semi-erect.
*Style color.*—Near RHS 155A.
*Style quantity.*—Average 19.
*Hair on ovary.*—Dense.
*Color of ovary.*—Near RHS White 155A.
*Number of sepals.*—6 to 8.
*Color of sepals.*—Near RHS 144B.
*Sepal width.*—Approximately 1 cm.
*Sepal length.*—Approximately 1.4 cm.
*Sepal texture.*—Smooth.
*Sepal shape.*—Deltate.
*Sepal margin.*—Entire.
*Sepal apex.*—Acute.
*Sepal base.*—Truncate.
Peduncle:
*Length.*—Average 7 cm.
*Diameter.*—Average 0.5 cm.

*Color.*—Near RHS 144B.
*Texture.*—Smooth.

FRUIT

*Average weight.*—160 grams.
*Minimum weight.*—135 grams.
*Maximum weight.*—201 grams.
*Average length.*—7 cm.
*Average diameter.*—5.3 cm.
*Color outer pericarp.*—Near RHS 5C.
*Color inner pericarp.*—Near RHS 4B.
*Core color.*—Near RHS 4B.
*Core diameter.*—Average 1 cm.
*General shape.*—Oblong.
*Brix at consumption.*—18.
*Brix at harvest.*—8.5 to 9.0.
*Fruit peduncle length.*—70 mm.
*Fruit peduncle width.*—23 mm.
*Median cross section.*—Circular.
*Stylar end shape.*—Weakly blunt protruding.
*Shoulder shape.*—Truncate.
*Calyx ring.*—Present.
*Calyx ring expression.*—Weak.
*Skin color at harvest.*—Near RHS 152B.
*Hair on fruit skin.*—Slightly downy.
*Hair adherence to skin.*—Weak.
*Skin adherence to flesh at maturity.*—Weak.
*Fruit core shape.*—Circular.
*Core-woody spike.*—Minor.
*Lenticels on fruit.*—None.
*Mature seed color.*—Black.
*Harvest time.*—Mid-late 25$^{th}$ April (Southern Hemisphere, Rangiriri, New Zealand).
*Overall cropping quantity.*—Heavy.
*Fruit Stem.*—Length: Average 6.5 to 7.5 cm. Diameter: Average 0.5 cm. Color: Near RHS 152D. Texture: Smooth.

OTHER CHARACTERISTICS

Storage life: Storage life is a minimum of 100 days at 2° C.
Disease/pest resistance: Neither resistance nor susceptibility to pathogens and pests common to *Actinidia chinensis* have been observed.
Temperature tolerance: Tolerates low temperatures to approximately −5° C. without negative effects, tolerates high temperatures to approximately 35° C. without negative effects.

What is claimed is:

1. A new and distinct cultivar of *Actinidia chinensis* plant named 'KZ02' as herein illustrated and described.

* * * * *